(12) United States Patent
Chung et al.

(10) Patent No.: US 8,513,479 B2
(45) Date of Patent: Aug. 20, 2013

(54) ZINC FERRITE CATALYSTS, METHOD OF PREPARING THEREOF AND METHOD OF PREPARING 1,3-BUTADIENE USING THEREOF

(75) Inventors: Young Min Chung, Daejeon (KR); Seong Jun Lee, Daejeon (KR); Tae Jin Kim, Daejeon (KR); Seung Hoon Oh, Seoul (KR); Yong Seung Kim, Daejeon (KR); In Kyu Song, Seoul (KR); Hee Soo Kim, Seoul (KR); Ji Chul Jung, Seoul (KR); Ho Won Lee, Seoul (KR)

(73) Assignees: SK Global Chemical Co., Ltd, Seoul (KR); SK Innovation Co., Ltd., Seoul (KR)

( * ) Notice: Subject to any disclaimer, the term of this patent is extended or adjusted under 35 U.S.C. 154(b) by 367 days.

(21) Appl. No.: 12/451,010

(22) PCT Filed: May 8, 2008

(86) PCT No.: PCT/KR2008/002587
§ 371 (c)(1),
(2), (4) Date: Oct. 20, 2009

(87) PCT Pub. No.: WO2008/140213
PCT Pub. Date: Nov. 20, 2008

(65) Prior Publication Data
US 2010/0121123 A1    May 13, 2010

(30) Foreign Application Priority Data
May 10, 2007 (KR) .................. 10-2007-0045499

(51) Int. Cl.
*C07C 5/333*  (2006.01)
(52) U.S. Cl.
USPC .......... 585/629; 585/616; 585/631; 585/625; 585/615; 502/329
(58) Field of Classification Search
USPC .......... 585/629, 616, 631, 625, 615; 502/329
See application file for complete search history.

(56) References Cited

U.S. PATENT DOCUMENTS

| 3,303,235 | A | * | 2/1967 | Croce et al. ............ | 585/618 |
| 3,387,053 | A | | 6/1968 | Lee | |
| 3,925,498 | A | * | 12/1975 | Stadig ................ | 585/625 |
| 3,937,748 | A | * | 2/1976 | Miklas ................ | 585/443 |
| 3,998,760 | A | | 12/1976 | Christmann | |
| 4,020,120 | A | * | 4/1977 | Christmann et al. ...... | 585/625 |

OTHER PUBLICATIONS

Toledo-Antonio, JA et al., Applied Catalysis A: General, (2002) vol. 234 pp. 137-144.*
R.J. Rennard and W.L. Kehl, "Oxidative Dehydrogenation of Butenes over Ferrite Catalysts", Journal of Catalysis 21, 282-293 (1971), Gulf Research & Development Company, Pittsburgh, Pennsylvania.
Yu M. Bakshi et al., "Catalytic Properties of System $SnO_2:Sb_2O_4$ in the Oxidative Dehydrogenation of n-Butenes to Butadiene", L. Ya. Karpov Physiochemical Institute, 1966, 177-185.
A.C.A.M. Bleijenberg et al., "Catalytic Oxidation of 1-Butene Over Bismuth Molybdate Catalysts, I. The System $Bi_2O_3$-$MoO_3$", Journal of Catalysis 4, 581-585 (1965), Department of Inorganic Chemistry, Technological University, Eindhoven, The Netherlands.
W.J. Linn and A.W. Sleight, "Oxidation of 1-Butene over Bismuth Molybdates and Bismuth Iron Molybdate", Journal of Catalysis 41, 134-139 (1976), Central Research and Development Department, E. I. du Pont de Nemours and Company, Wilmington, Delaware.
Guo Hongda et al, Research on Reduction-Oxidization Performance of Ferrate Catalyst for Preparing Butadiene by Oxidative Dehydrogenation of Butene, Petrochemical Industry, vol. 13, No. 9, pp. 573-578 dated Dec. 31, 1984. (Abstract).
Second Notification of Office Action from the State Intellectual Property Office of P.R. China regarding Application No. 200880014941.3 (SK Innovation Co., Ltd.; SK Global Chemical Co.; Ltd.); dated Jun. 29, 2012.
Japanese Office Action dated Nov. 28, 2012 regarding U.S. Appl. No. 12/451,101.
Toledo-Antonio, J.A., et al.; "Correlation between the magnetism of non-stoichiometric zinc ferrites and their catalytic activity for oxidative dehydrogenation of 1-butene"; Applied Catalysis A: General, Aug. 8, 2002; vol. 234, No. 1-2, p. 137-144.

* cited by examiner

*Primary Examiner* — In Suk Bullock
*Assistant Examiner* — Sharon Pregler
(74) *Attorney, Agent, or Firm* — Abelman, Frayne & Schwab

(57) ABSTRACT

The present invention relates to a zinc ferrite catalyst, a method of producing the same, and a method of preparing 1,3-butadiene using the same. Specifically, the present invention relates to a zinc ferrite catalyst which is produced in a pH-adjusted solution using a coprecipitation method, a method of producing the same, and a method of preparing 1,3-butadiene using the same, in which the 1,3-butadiene can be prepared directly using a C4 mixture including n-butene and n-butane through an oxidative dehydrogenation reaction. The present invention is advantageous in that 1,3-butadiene can be obtained at a high yield directly using a C4 fraction without performing an additional process for separating n-butene, as a reactant, from a C4 fraction containing impurities.

3 Claims, 2 Drawing Sheets

ZINC FERRITE CATALYSTS, METHOD OF PREPARING THEREOF AND METHOD OF PREPARING 1,3-BUTADIENE USING THEREOF

TECHNICAL FIELD

The present invention relates to a zinc ferrite catalyst, a method of producing the same, and a method of preparing 1,3-butadiene using the same. Specifically, the present invention relates to a zinc ferrite catalyst, which is produced in a pH-adjusted solution using a coprecipitation method, and which can prepare high value-added 1,3-Butadiene using a cheap C4 mixture containing impurities, such as n-butane, n-butene, and the like, as reactants without requiring that an additional n-butane separation process or n-butene extraction process be performed, a method of producing the same, and a method of preparing 1,3-butadiene using the same.

BACKGROUND ART 1,3-butadiene, the demand for which is increasing in petrochemical markets, is produced through a naphtha cracking process, a direct n-butene dehydrogenation reaction, or an oxidative n-butene dehydrogenation reaction, and is then supplied to a petrochemical market. Among them, the naphtha cracking process accounts for 90% or more of butadiene supply, but is problematic in that new naphtha cracking centers (NCCs) must be established in order to meet the increasing demand for butadiene, and in that other basic fractions, as well as butadiene, are excessively produced because the naphtha cracking process is not a process for producing only butadiene. Further, the direct n-butene dehydrogenation reaction is problematic in that it is thermodynamically disadvantageous, and in that high-temperature and low-pressure conditions are required because it is an endothermic reaction, so that the yield is very low, with the result that it is not suitable for a commercial process [L. M. Madeira, M. F. Portela, Catal. Rev., volume 44, page 247 (2002)].

The oxidative n-butene dehydrogenation reaction, which is a reaction for forming 1,3-butadiene and water by reacting n-butene with oxygen, is advantageous in that, since stable water is formed as a product, the reaction is thermodynamically favorable, and the reaction temperature can be lowered. Therefore, a process of producing 1,3-butadiene through the oxidative n-butene dehydrogenation reaction can be an effective alternative process for producing only butadiene. In particular, when a C4-raffinate-3 mixture or a C4 mixture containing impurities, such as n-butane and the like, is used as a supply source of n-butene, there is an advantage in that excess C4 fractions can be made into high value-added products. Specifically, the C4-raffinate-3 mixture, which is a reactant used in the present invention, is a cheap C4 fraction obtained by separating useful compounds from a C4 mixture produced through naphtha cracking. More specifically, a C4-raffinate-1 mixture is a mixture obtained by separating 1,3-butadiene from a C4 mixture produced through naphtha cracking, a C4-raffinate-2 mixture is a mixture obtained by separating iso-butylene from the C4-raffinate-1 mixture, and a C4-raffinate-3 mixture is a mixture obtained by separating 1-butene from the C4-raffinate-2 mixture. Therefore, the C4-raffinate-3 mixture or C4 mixture mostly includes 2-butene (trans-2-butene and cis-2-butene), n-butane, and 1-butene.

As described above, the oxidative dehydrogenation reaction of n-butene (1-butene, trans-2-butene, cis-2-butene) is a reaction for forming 1,3-butadiene and water by reacting n-butene with oxygen. However, in the oxidative dehydrogenation reaction of n-butene, many side reactions, such as complete oxidation, etc., are predicted because oxygen is used as a reactant. For this reason, it is very important to develop a catalyst which can suppress these side reactions to the highest degree and has high selectivity for 1,3-butadiene. Examples of catalysts currently used for the oxidative dehydrogenation reaction of n-butene include a ferrite-based catalyst [M. A. Gibson, J. W. Hightower, J. Catal., volume 41, page 420 (1976)/W. R. Cares, J. W. Hightower, J. Catal., volume 23, page 193 (1971)/R. J. Rennard, W. L. Kehl, J. Catal., volume 21, page 282 (1971)], a tin-based catalyst [Y. M. Bakshi, R. N. Gur'yanova, A. N. Mal'yan, A. I. Gel'bshtein, Petroleum Chemistry U.S.S.R., volume 7, page 177 (1967)], a bismuth molybdate-based catalyst [A. C. A. M. Bleijenberg, B. C. Lippens, G. C. A. Schuit, J. Catal., volume 4, page 581 (1965)/Ph. A. Batist, B. C. Lippens, G. C. A. Schuit, J. Catal., volume 5, page 55 (1966)/W. J. Linn, A. W. Sleight, J. Catal., volume 41, page 134 (1976)/R. K. Grasselli, Handbook of Heterogeneous Catalysis, volume 5, page 2302 (1997)] and the like.

Among them, the ferrite-based catalyst has a spinel structure of $AFe_2O_4$ (A=Zn, Mg, Mn, Co, Cu, and the like). It is known that the ferrite having such a spinel structure can be used a catalyst for an oxidative dehydrogenation reaction through the oxidation and reduction of iron ions and the interaction of oxygen ions and gaseous oxygen in crystals [M. A. Gibson, J. W. Hightower, J. Catal., volume 41, page 420 (1976)/R. J. Rennard, W. L. Kehl, J. Catal., volume 21, page 282 (1971)]. The catalytic activities of ferrite-based catalysts are different from each other depending on the kind of metals constituting the bivalent cation sites of the spinel structure. Among them, zinc ferrite, magnesium ferrite and manganese ferrite are known to exhibit good catalytic activity in the oxidative dehydrogenation reaction of n-butene, and, particularly, zinc ferrite is reported to have higher selectivity for 1,3-butadiene than other metal ferrites [F.-Y. Qiu, L.-T. Weng, E. Sham, P. Ruiz, B. Delmon, Appl. Catal., volume 51, page 235 (1989)].

It was reported in several patent documents that zinc ferrite-based catalysts were used in the oxidative dehydrogenation reaction of n-butene. Specifically, in relation to the fact that 1,3-butadiene is produced through the oxidative dehydrogenation reaction of n-butene using pure zinc ferrite made by a coprecipitation method, it was reported that the oxidative dehydrogenation reaction of 2-butene was conducted using a zinc ferrite catalyst having a pure spinel structure at 375° C., thus obtaining a yield of 41% [R. J. Rennard, W. L. Kehl, J. Catal., volume 21, page 282 (1971)]. Further, it was reported that 1,3-butadiene was obtained at a yield of 21% at 420° C. through an oxidative dehydrogenation reaction, in which 1-butene was used as a reactant and a zinc ferrite catalyst was used [J. A. Toledo, P. Bosch, M. A. Valenzuela, A. Montoya, N. Nava, J. Mol. Catal. A, volume 125, page 53 (1997)].

Further, methods of manufacturing a zinc ferrite catalyst, by which 1,3-butadiene can be produced at a higher yield through pre-treatment and post-treatment, performed in order to increase the activity of a zinc ferrite catalyst in an oxidative dehydrogenation reaction, was disclosed in several patent documents [F.-Y. Qiu, L.-T. Weng, E. Sham, P. Ruiz, B. Delmon, Appl. Catal., volume 51, page 235 (1989)/L. J. Crose, L. Bajars, M. Gabliks, U.S. Pat. No. 3,743,683 (1973)/J. R. Baker, U.S. Pat. No. 3,951,869 (1976)].

In addition to the above methods of manufacturing a zinc ferrite catalyst, in order to increase the activity of a catalyst in the oxidative dehydrogenation reaction of n-butene, the oxidative dehydrogenation reaction of n-butene was conducted using a catalyst in which a zinc ferrite catalyst is physically mixed with other metal oxides [W.-Q. Xu, Y.-G. Yin, G.-Y. Li, S. Chen, Appl. Catal. A, volume 89, page 131 (1992)].

The zinc ferrite catalyst, reported in the above patent documents, is single-phase zinc ferrite or a catalyst system including the single-phase zinc ferrite as a central component, and the zinc ferrite, which is a central component acting on the oxidative dehydrogenation reaction of n-butene, is chiefly prepared using a coprecipitation method. As a typical example of a method of preparing zinc ferrite using a coprecipitation method, there is a method of adding an aqueous zinc precursor solution and an aqueous iron precursor solution to an excess aqueous reductant solution [L. J. Crose, L. Bajars, M. Gabliks, U.S. Pat. No. 3,743,683 (1973)/J. R. Baker, U.S. Pat. No. 3,951,869 (1976)].

In addition to the methods of increasing the activity of the zinc ferrite catalyst through pre-treatment and post-treatment or mixing, clearly set forth in the above patent documents, as an attempt to increase the activity of the catalyst itself, a method of substituting zinc or iron, which is a component of zinc ferrite, with other metals has also been reported in patent documents. It was disclosed in this method that, in a catalyst in which other metals, instead of iron, are disposed at trivalent iron ion sites of ferrite having a spinel structure, the activity of the catalyst is changed due to the presence of the other metals. In particular, it was reported in a document that, when a catalyst substituted with chromium or aluminium was used, catalytic activity was increased [J. A. Toledo, P. Bosch, M. A. Valenzuela, A. Montoya, N. Nava, J. Mol. Catal. A, volume 125, page 53 (1997)].

In the oxidative hydrogenation reaction of n-butene, when the zinc ferrite catalyst substituted with other metals or the mixed-phase catalyst is used, high activity can be obtained in the production of 1,3-butadiene, compared to when a conventional zinc ferrite catalyst is used, but there is a problem in that it is difficult to synthesize the above catalyst, and it is also difficult to reproduce the above catalyst, and thus it is difficult to commercialize the above catalyst. Further, since a C4 mixture, which is a reactant used in the present invention, includes various components as well as n-butene, when the above catalyst is used, there is a problem in that catalytic activity and selectivity for 1,3-butadiene may be greatly changed due to side reactions.

The oxidative dehydrogenation reaction of n-butene has another problem in that, when a reactant includes n-butane in a predetermined amount or more, the yield of 1,3-butadiene is decreased [L. M. Welch, L. J. Croce, H. F. Christmann, Hydrocarbon Processing, page 131 (1978)]. Therefore, in the above conventional technologies, an oxidative dehydrogenation reaction is conducted using only pure n-butene (1-butene or 2-butene) as a reactant, thus solving such problems. In practice, reactants containing no n-butane are used even in commercial processes using a ferrite catalyst. As disclosed in the above patent documents, in the catalyst and process for preparing 1,3-butadiene from n-butene through an oxidative dehydrogenation reaction, since pure n-butene is used as a reactant, an additional process of separating pure n-butene from a C4 mixture is required, thus inevitably decreasing economic efficiency.

As described above, in the conventional catalysts and processes for preparing 1,3-butadiene through the oxidative dehydrogenation reaction of n-butene, 1,3-butadiene is prepared using pure n-butene as a reactant through a mixed-phase, substituted or modified zinc ferrite catalyst. However, an example in which 1,3-butadiene was prepared using a C4-raffinate-3 mixture or a C4 mixture including various components as well as n-butane having a high concentration on a pure single-phase zinc ferrite catalyst without performing additional pre-treatment or post-treatment and metal substitution procedure has never been reported.

DISCLOSURE

Technical Problem

Therefore, in order to overcome the above problems, the present inventors found that, when a pure single-phase zinc ferrite catalyst, produced in a pH-adjusted solution using a coprecipitation method, is used, 1,3-butadiene can be prepared on the zinc ferrite catalyst using a cheap C4 mixture including n-butane and n-butene as a reactant through an oxidative dehydrogenation reaction without performing an additional n-butene separation process. Based on this finding, the present invention was completed.

Accordingly, the present invention has been made keeping in mind the above problems occurring in the prior art, and an object of the present invention is to provide a method of producing a zinc ferrite catalyst for preparing 1,3-butadiene, which has a simple structure, and can be easily synthesized and reproduced.

Another object of the present invention is to provide a method of preparing 1,3-butadiene by performing an oxidative dehydrogenation reaction on the zinc ferrite catalyst produced through the method directly using a C4 mixture as a reactant without performing an additional n-butene separation process.

Technical Solution

In order to accomplish the above objects, an aspect of the present invention provides a method of producing a zinc ferrite catalyst for preparing 1,3-butadiene, including: (A) dissolving a zinc precursor and an iron precursor in distilled water to form an aqueous precursor solution; (B) mixing the aqueous precursor solution with an alkaline solution to form a mixed solution and simultaneously adjusting the pH of the mixed solution within the range of 6~10; (C) filtering the pH-adjusted mixed solution to obtain a solid catalyst; (D) drying the solid catalyst at 70~200° C.; and (E) heat-treating the dried solid catalyst at 350~800° C.

Another aspect of the present invention provides a method of preparing 1,3-butadiene, including: (A) providing a mixed gas of a C4 mixture, air and steam as a reactant; (B) continuously passing the reactant through a catalyst layer supported with the catalyst prepared using the above method to conduct an oxidative dehydrogenation reaction; and (C) obtaining 1,3-butadiene from the catalyst layer.

Advantageous Effects

According to the present invention, a zinc ferrite catalyst, having a simple structure and synthesis procedure and high reproducibility, can be obtained. When the zinc ferrite catalyst is used, 1,3-butadiene can be prepared directly using a C4 mixture including n-butane at a high concentration as a reactant through an oxidative hydrogenation reaction without performing an additional n-butane separation process, and 1,3-butadiene, having high activity, can be also obtained at a high yield.

Further, according to the present invention, since 1,3-butadiene, which is highly useful in the petrochemical industry, can be prepared from a C4 mixture or a C4 raffinate-3 mixture, which is of little use, a C4 fraction can be highly value-added. In addition, a process for producing only 1,3-butadiene without newly establishing a naphtha cracking center (NCC) can be secured, so that the demand for 1,3-butadiene can be met, thereby improving economic efficiency compared to conventional processes.

BEST MODE

Figure 1:
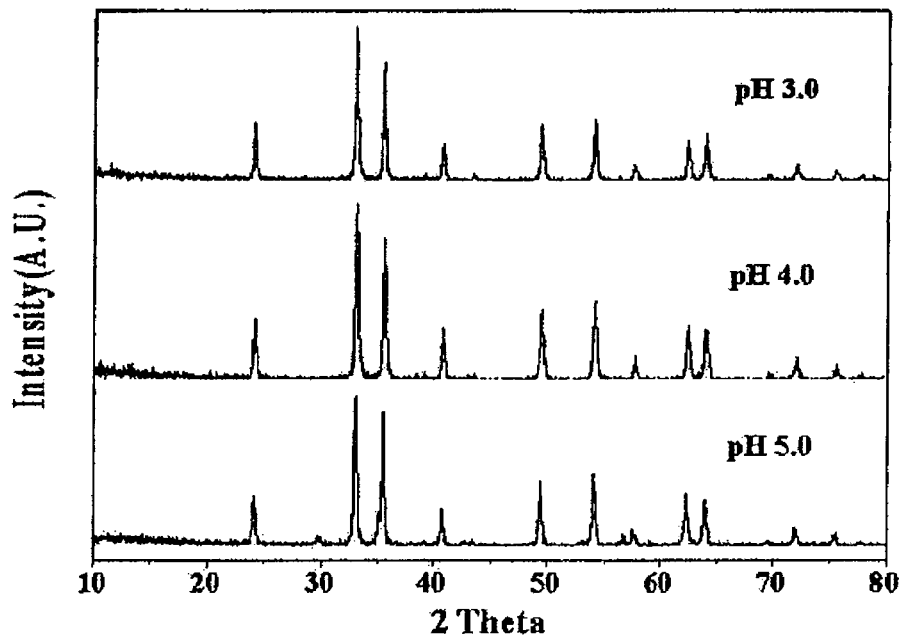
FIG. 1 is a graph showing the results of X-ray diffraction analysis of three kinds of zinc ferrite catalysts according to Preparation Example of the present invention.

Hereinafter, the present invention will be described in detail.

As described above, the present invention provides a method of producing a single-phase zinc ferrite catalyst in a pH-adjusted solution using a coprecipitation method, and a method of preparing 1,3-butadiene through the oxidative dehydrogenation of n-butene using the produced single-phase zinc ferrite catalyst. In the method of preparing 1,3-butadiene, 1,3-butadiene can be prepared using a C4 mixture as a reactant without performing an additional n-butane separation process.

A single-phase zinc ferrite catalyst is used as a catalyst for preparing 1,3-butadiene of the present invention in order to obtain 1,3-butadiene at high yield in the oxidative dehydrogenation reaction of n-butene. The characteristics of the single-phase zinc ferrite catalyst are changed depending on the catalyst preparation conditions, and thus the activity thereof is also changed. In the present invention, a zinc ferrite catalyst, exhibiting high activity in the oxidative dehydrogenation reaction of n-butene through precise pH adjustment, was prepared.

As a zinc precursor and an iron precursor for preparing the zinc ferrite catalyst, commonly-used precursors may be used. Examples of the precursors may include chloride precursors and nitrate precursors.

The amount of the zinc precursor and iron precursor is adjusted such that the iron/zinc atom number ratio thereof is 1.5~2.5. Subsequently, the zinc precursor and iron precursor are each dissolved in distilled water and then mixed with each other to form an aqueous precursor solution. In this case, when the iron/zinc atom number ratio deviates from the range of 1.5~2.5, zinc cannot easily infiltrate into an iron lattice, or the catalytic activity becomes low. Meanwhile, in order to coprecipitate zinc ferrite, an alkaline solution having a molar concentration of 1.5~4.0 M, for example, an aqueous sodium hydroxide solution having a molar concentration of 3 M, is additionally prepared. When the molar concentration of the alkaline solution is below 1.5 M, it is difficult to form a ferrite structure, and when the molar concentration thereof is above 4.0 M, it is difficult to remove metal ions bonded with hydroxide groups, for example, sodium (Na) ions in the case of sodium hydroxide at the time of washing, thus decreasing catalytic activity. The alkaline solution may be prepared using other bases in addition to sodium hydroxide, but it is preferred that the alkaline solution be prepared using sodium hydroxide in order to increase catalytic activity and to obtain a ferrite structure having high crystallinity and a pure ferrite phase.

The aqueous precursor solution is injected into distilled water using a syringe in order to obtain zinc ferrite from the zinc precursor and iron precursor. In this case, when the alkaline solution is injected thereinto together with the aqueous precursor solution, a coprecipitation solution is formed, and the pH of the precipitation solution can be adjusted and maintained within a range of 6~10. The coprecipitation solution is sufficiently stirred for 2~12 hours, and preferably 6~12 hours.

The stirred coprecipitation solution is sufficiently phase-separated such that a solid catalyst is precipitated, and then the precipitated solid catalyst is obtained using a pressure-sensitive filter.

The obtained solid catalyst is dried at 70~200° C., and preferably 120~180° C. Subsequently, the dried solid catalyst is put into an electric furnace, and is then heat-treated at 350~800° C., and preferably 500~700° C., to prepare a pure single-phase zinc ferrite catalyst.

According to the present invention, a zinc ferrite catalyst separates hydrogen atoms from n-butene while reacting with gaseous oxygen adsorbed with iron ions in a catalyst lattice and n-butene, and additionally separates hydrogen atoms therefrom through the interaction between oxygen and iron ions in the catalyst lattice, thus forming butadiene and water. That is, the oxidative dehydrogenation reaction of n-butene is conducted according to such a mechanism. Therefore, the characteristics of the iron ions and oxygen in the catalyst lattice influence the activity in the oxidative dehydrogenation reaction of n-butene. Further, since the phase characteristics of the zinc ferrite catalysts formed under different conditions are different from each other, the catalysts, prepared by adjusting the pH of the coprecipitation solution in the present invention, exhibit different activities from each other.

According to Preparation Example 1 of the present invention, as the result of comparing the phase characteristics of the catalysts coprecipitated at different pH with each other through X-ray diffraction analysis, it was found that the characteristics of the catalyst lattice change depending on the pH of the coprecipitation solution. Specifically, it was found that, in the case of the catalyst coprecipitated at a pH of 3~5, $\alpha$-iron oxide(III) ($\alpha$-$Fe_2O_3$)(III)), known to have low selectivity for 1,3-butadiene due to the complete oxidation in the oxidative dehydrogenation reaction of n-butene, rather than zinc ferrite, is chiefly formed, and thus the catalyst is not suitable as a catalyst for the present invention. In contrast, it was found that, in the case of the catalyst coprecipitated at a pH of 6, zinc ferrite is chiefly formed, and, in the case of the catalyst coprecipitated at a pH of 7~12, single-phase zinc ferrite is formed (referring to FIGS. 1 to 3).

Therefore, preferably, the catalyst for preparing 1,3-butadiene of the present invention is a single-phase zinc ferrite catalyst coprecipitated by adjusting the pH of a coprecipitation solution within the range of 6~10, but, more preferably, is prepared by adjusting the pH of a coprecipitation solution within the range of 8~9 in consideration of catalytic activity.

Further, the present invention provides a method of preparing 1,3-butadiene using a C4 mixture or a C4-raffinate-3 mixture on the zinc ferrite catalyst formed at the fixed pH through an oxidative dehydrogenation reaction without performing an additional n-butane separation process in order to supply n-butene.

According to Experimental Examples of the present invention, a catalytic reaction is conducted by fixing catalyst powder in a linear Pyrex reactor, and installing the linear Pyrex reactor in an electric furnace, thus maintaining the reaction temperature of the catalyst layer constant, and then continuously passing reactants through the catalyst layer in the linear Pyrex reactor.

The reaction temperature for conducting an oxidative dehydrogenation reaction is maintained at 300~600° C., preferably 350~500° C., and more preferably 420° C. The amount of the catalyst is set such that the gas hourly space velocity (GHSV) of the reactant is 50~5000 $h^{-1}$, preferably 100~1000 $h^{-1}$, and more preferably 300~600 $h^{-1}$, based on n-butene. The reactant is mixed gas of a C4 mixture, air and steam, and the mixing volume ratio of n-butene:air:steam in the reactant is 1:0.5~10:1~50, and preferably 1:3~4:10~30. When the mixing volume ratio thereof deviates from this range, desired butadiene yield cannot be obtained, and safety problems may occur due to a rapid exothermic reaction, which is undesirable.

In the present invention, n-butene and oxygen, which are reactants for an oxidative dehydrogenation reaction, are supplied in the form of mixed gas. A C4 mixture or a C4-raffinate-3 mixture, which is a supply source of n-butene, and air, which is another reactant, are supplied in precisely adjusted amounts using a mass flow controller. Steam, known to be effective in removing the reaction heat caused by an oxidative dehydrogenation reaction and improve selectivity for 1,3-butadiene, is supplied into a reactor by injecting liquid-phase water using a syringe pump and simultaneously vaporizing it. That is, the temperature of a water inlet in the reactor is maintained at 150~300° C., and preferably 180~250° C., so that the water injected into the reactor using the syringe pump is immediately vaporized, with the result that the vaporized water is mixed with other reactants (C4 mixture and air) and simultaneously passes through a catalyst layer in the reactor.

Among the reactants of the present invention, the C4 mixture includes 0.5~50 wt % of n-butane, 40~99 wt % of n-butene, and 0.5~10 wt % of a balance thereof, which is a C4 mixture other than the n-butane and n-butene. Examples of constituents of the balance include iso-butane, cyclobutane, methyl cyclobutane, iso-butene, and the like.

When the zinc ferrite catalyst of the present invention is used, 1,3-butadiene can be produced from n-butene included in a reactant at a high yield by performing an oxidative dehydrogenation reaction using a cheap C4 mixture or C4-raffinate-3 mixture including n-butene as the reactant. In particular, even when a C4 mixture including a large amount of n-butane, known to suppress the oxidative dehydrogenation reaction of n-butene, is directly used as a reactant, high activity and high selectivity for 1,3-butadiene can be obtained.

Further, the present invention is advantageous in that the zinc ferrite catalyst of the present invention is prepared using a direct catalyst synthesis technology, rather than subsidiary technologies, such as conventional catalytic substitution or catalytic treatment, so that the composition of the zinc ferrite catalyst and the synthesis procedure thereof are simple, with the result that the zinc ferrite catalyst is easily synthesized, and 1,3-butadiene can be produced from a C4 mixture or C4-raffinate-3 mixture containing impurities at high yield.

MODE FOR INVENTION

Hereinafter, the present invention will be described in more detail with reference to the following Examples, but the scope of the present invention is not limited thereto.

Preparation Example 1

Determination of Precursor and Solvent for Producing a Zinc Ferrite Catalyst

Zinc chloride ($ZnCl_2$) was used as a zinc precursor, and iron chloride hexahydrate ($FeCl_3.6H_2O$) was used as an iron precursor. The zinc precursor and iron precursor, which are materials easily dissolved in distilled water, were each dissolved in distilled water and then mixed with each other to form an aqueous precursor solution. A predetermined amount of distilled water was provided as a medium for coprecipitation, and then the aqueous precursor solution was added into the distilled water and simultaneously a predetermined amount of an aqueous sodium hydroxide solution was added thereinto to adjust the pH, so as to form a mixed solution. At this time, in order to accurately adjust the pH, the aqueous precursor solution and aqueous sodium hydroxide solution slowly were dropped onto the distilled water. In order to obtain a sample having a uniform composition, the mixed solution was sufficiently stirred using a magnetic stirrer.

Production of Zinc Ferrite ($ZnFe_2O_4$) Catalyst 1.42 g of zinc chloride and 5.61 g of iron chloride hexahydrate were dissolved in distilled water (100 ml), mixed with each other and then sufficiently stirred to form an aqueous precursor solution. Subsequently, after it was confirmed that precursors were completely dissolved in distilled water, the aqueous precursor solution was dropped onto distilled water (100 ml), and simultaneously, an aqueous sodium hydroxide solution having a concentration of 3 M was added thereinto in order to adjust the pH and coprecipitate the precursors to form a mixed solution, and the mixed solution was adjusted such that the pH of the precipitation solution was 3, 4, 5, 6, 7, 8, 9, 10, 11 or 12.

Figure 2:
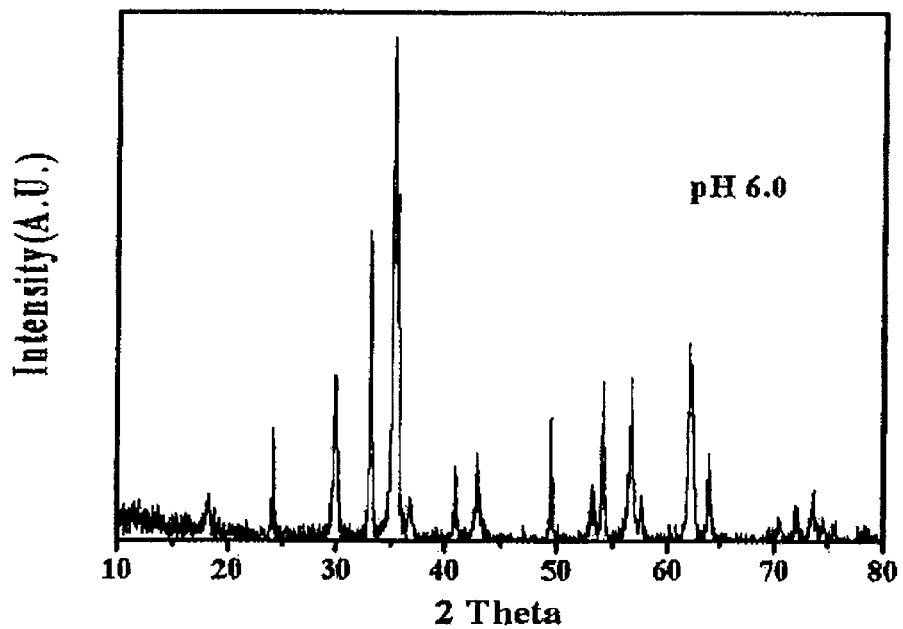
FIG. 2 is a graph showing the result of X-ray diffraction analysis of a kind of zinc ferrite catalyst according to Preparation Example of the present invention.
Figure 3:
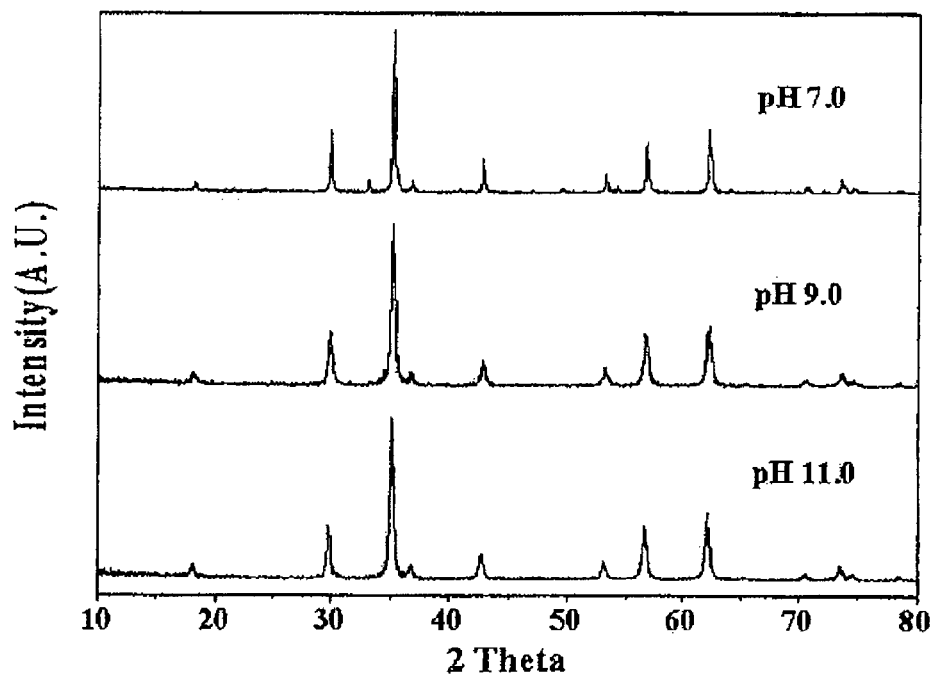
FIG. 3 is a graph showing the results of X-ray diffraction analysis of three kinds of zinc ferrite catalysts according to Preparation Example of the present invention.

The mixed solution was sufficiently stirred using a magnetic stirrer at room temperature for 12 hours, and was then left at room temperature for 12 hours for phase separation. Subsequently, the mixed solution was filtered using a pressure-sensitive filter to obtain a solid sample, and the obtained solid sample was dried at 175° C. for 16 hours. The dried solid sample was heat-treated in an electric furnace at a temperature of 650° C. under an air atmosphere, thus producing a single-phase α-iron oxide (α-$Fe_2O_3$) catalyst, a single-phase zinc ferrite catalyst and a catalyst having a mixed phase of the two. The phase of the produced catalyst was confirmed through X-ray diffraction analysis, and the results thereof are shown in FIGS. 1 to 3. From FIG. 1, it can be seen that, in a catalyst precipitated at a low pH of 3~5, α-iron oxide (α-$Fe_2O_3$) phase, rather than a zinc ferrite phase, was formed. From FIG. 2, it can be seen that, in a catalyst precipitated at a pH of 6, a zinc ferrite phase was chiefly formed, but an α-iron oxide (α-$Fe_2O_3$) phase was also partially formed. From FIG. 3, it can be seen that, in a catalyst precipitated at a high pH of more than 7, only a single zinc ferrite phase was chiefly formed.

Example 1

Oxidative Dehydrogenation Reaction of C4-Raffinate-3 Mixture or C4 Mixture on Zinc Ferrite Catalyst The oxidative dehydrogenation reaction of n-butene was conducted using the zinc ferrite catalyst produced in Preparation Example 1 under the following experimental conditions.

In the present invention, a C4 mixture was used as a reactant in the oxidative dehydrogenation reaction of n-butene, and the composition thereof is shown in Table 1. The C4 mixture, which is a reactant, was introduced into a reactor in the form of mixed gas together with air and steam, and a linear Pyrex fixed-bed reactor was used as the reactor.

The composition ratio of the reactant was set based on the amount of n-butene in the C4 mixture, and was set such that the mixing ratio of n-butene:air:steam was 1:3.75:15. Steam, which was formed by vaporizing liquid-phase water, was mixed with other reactants, such as the C4 mixture and air, and then introduced into the reactor. The amount of the C4 mixture and air was controlled using a mass flow controller, and the amount of steam was controlled by controlling the flow rate of the liquid-phase water using a syringe pump.

The oxidative dehydrogenation reaction of n-butene was conducted by setting the amount of catalyst such that the gas hourly space velocity (GHSV), as the flow rate of the reactant, was 475 $h^{-1}$, based on the amount of n-butene in the C4 mixture, and the temperature of the catalyst layer in the fixed-bed reactor, as a reaction temperature, was maintained at 420° C. The product obtained after the reaction included carbon dioxide, which is a side-product obtained through complete oxidation, side-products obtained through cracking, side-products obtained through isomerization, and n-butane included in the reactant, in addition to targeted 1,3-butadiene. The product was analyzed using gas chromatography. In the oxidative dehydrogenation reaction of n-butene, the conversion rate of n-butene, selectivity for 1,3-butadiene and yield of 1,3-butadiene through the zinc ferrite catalyst were calculated using the following Mathematical Formulae, respectively.

$$\text{Conversion rate (\%)} = \frac{\text{Number of moles of reacted } n\text{-butene}}{\text{Number of moles of supplied } n\text{-butene}} \times 100 \quad [\text{Mathematical Formula 1}]$$

$$\text{Selectivity (\%)} = \frac{\text{Number of moles of formed 1,3-butadiene}}{\text{Number of moles of reacted } n\text{-butene}} \times 100 \quad [\text{Mathematical Formula 2}]$$

$$\text{Yield (\%)} = \frac{\text{Number of moles of formed 1,3-butadiene}}{\text{Number of moles of supplied } n\text{-butene}} \times 100 \quad [\text{Mathematical Formula 3}]$$

TABLE 1

Composition of C4 mixture used as reactant

| Composition | Molecular formulae | Wt % |
|---|---|---|
| i-butane | $C_4H_{10}$ | 0.07 |
| n-butane | $C_4H_{10}$ | 41.57 |
| methyl cyclopropane | $C_4H_8$ | 0.09 |
| trans-2-butane | $C_4H_8$ | 33.94 |
| 1-butene | $C_4H_8$ | 7.52 |
| isobutylene | $C_4H_8$ | 0.02 |
| cis-2-butene | $C_4H_8$ | 16.48 |
| cyclobutane | $C_4H_8$ | 0.29 |
| i-pentane | $C_5H_{12}$ | 0.02 |
| total | | 100.00 |

Experimental Example 1

Activity of α-Iron Oxide (α-$Fe_2O_3$) Catalyst

As the result of X-ray diffraction analysis, among the catalysts produced in Preparation Example 1, in the catalyst coprecipitated at a pH of 3, 4 and 5, it was found that α-iron oxide, rather than zinc ferrite, was formed (refer to FIG. 1). Three kinds of the α-iron oxide phase catalysts were applied to the oxidative dehydrogenation of a C4 mixture as in Example 1, and the results thereof are shown in Table 2. As reported in many documents, α-iron oxide had low activity in the oxidative dehydrogenation of n-butene in the present invention, and as the result of conducting an oxidative dehydrogenation reaction using the α-iron oxide, it can be seen that the conversion rate of n-butene was 17.0~42.8%, the selectivity for 1,3-butadiene was 45~77.0%, and the yield of 1,3-butadiene was 7.7~32.9%, and thus it was found that the activity of the α-iron oxide catalyst in an oxidative dehydrogenation reaction is very low.

TABLE 2

Activity of an α-iron oxide (α-$Fe_2O_3$) catalyst coprecipitated at pH of 3, 4, and 5

| pH at the time of the preparation of catalyst | Conversion rate of n-butene (%) | Selectivity for 1,3-butadiene (%) | Yield of 1,3-butadiene (%) |
|---|---|---|---|
| 3 | 17.0 | 45.0 | 7.7 |
| 4 | 30.4 | 68.7 | 20.9 |
| 5 | 42.8 | 77.0 | 32.9 |

Experimental Example 2

Activity of Mixed-Phase Catalyst of Zinc Ferrite and α-Iron Oxide (α-$Fe_2O_3$)

As the result of observing the phase of the catalyst coprecipitated at a pH of 6 using the same method as in Preparation Example 1 through X-ray diffraction analysis, it was found that a mixed-phase of zinc ferrite and α-iron oxide was formed (refer to FIG. 2). The oxidative dehydrogenation of a C4 mixture was conducted using the catalyst coprecipitated at a pH of 6 as in Example 1, and the results thereof are shown in Table 3.

In a catalytic activity test conducted using the mixed-phase catalyst prepared at a pH of 6, it was found that the conversion rate of n-butene was 76.1%, the selectivity for 1,3-butadiene was 94.1%, and the yield of 1,3-butadiene was 71.8%, and thus it can be seen that the activity of the mixed-phase catalyst of zinc ferrite and α-iron oxide in an oxidative dehydrogenation reaction was excellent.

TABLE 3

Activity of mixed-phase catalyst of zinc ferrite and α-iron oxide (α-$Fe_2O_3$)

| pH at the time of the preparation of catalyst | Conversion rate of n-butene (%) | Selectivity for 1,3-butadiene (%) | Yield of 1,3-butadiene (%) |
|---|---|---|---|
| 6 | 76.1 | 94.1 | 71.8 |

Experimental Example 3

Activity of Single-Phase Zinc Ferrite Catalyst

As the result of observing the phase of the catalyst coprecipitated at a pH of 7~12 using the same method as in Preparation Example 1 through X-ray diffraction analysis, it was found that a single-phase of zinc ferrite was formed (refer to FIG. 3). The oxidative dehydrogenation of a C4 mixture was conducted using the six kinds of catalysts coprecipitated at a pH of 7~12 as in Example 1, and the results thereof are shown in Table 4.

It was found that the single-phase catalysts coprecipitated at a pH of 7~10 exhibited a conversion rate of n-butene of 78% or more, a selectivity for 1,3-butadiene of 92% or more, and a yield of 1,3-butadiene of 72% or more, and it was found that the single-phase catalysts coprecipitated in a strong basic atmosphere of a pH of 11 and 12 exhibited very low activity.

TABLE 4

Activity of single-phase zinc ferrite catalyst

| pH at the time of the preparation of catalyst | Conversion rate of n-butene (%) | Selectivity for 1,3-butadiene (%) | Yield of 1,3-butadiene (%) |
| --- | --- | --- | --- |
| 7 | 79.6 | 93.8 | 74.6 |
| 8 | 78.9 | 95.1 | 75.1 |
| 9 | 82.8 | 94.2 | 78.2 |
| 10 | 78.3 | 92.8 | 72.6 |
| 11 | 29.7 | 68.6 | 20.3 |
| 12 | 15.6 | 27.7 | 4.3 |

Experimental Example 4

Figure 4:
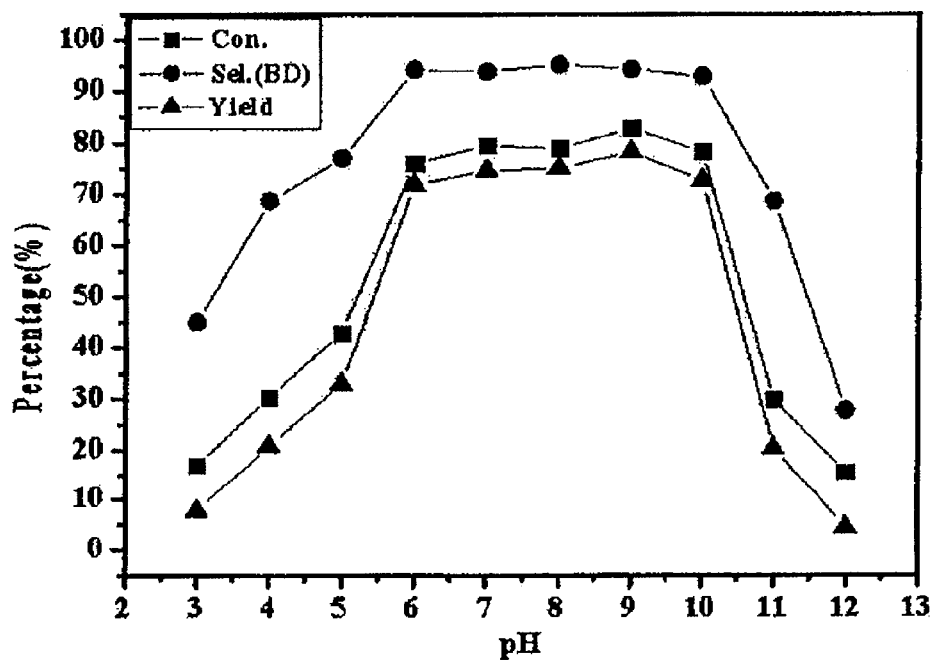
FIG. 4 is a graph showing the change in the activity of ten kinds of zinc ferrite catalysts depending on pH at the time of coprecipitation according to Experimental Example of the present invention.

Change in Activity of Zinc Ferrite Catalyst Depending on pH at the Time of Coprecipitation As the results of the tests for catalyst preparation and catalytic activity according to Preparation Example 1 and Experimental Examples 1 to 3, the effects of the pH of a coprecipitation solution on the activity of zinc ferrite are shown in FIG. 4. From FIG. 4, it was found that the activity of zinc ferrite is low at low pH due to the formation of α-iron oxide, but that the activity of zinc ferrite is high at a pH of 6~10 due to the increase in the formation of zinc ferrite according to the increase in pH. Further, it was observed that the activity of zinc ferrite is rapidly decreased at a pH higher than 10. The reason for this is determined to be that the zinc ferrite catalyst has 10~20 times more sodium content than that of the catalyst, exhibiting excellent activity as a result of element analysis, and thus the sodium present in a catalyst lattice negatively influences the activity of the catalyst.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing 1,3-butadiene, comprising:
 (i) producing a zinc ferrite catalyst consisting of:
  (A) dissolving a zinc precursor and an iron precursor in distilled water to form an aqueous precursor solution;
  (B) adding the aqueous precursor solution and simultaneously an alkaline solution having a molar concentration of 1.5-4.0 M to distilled water to form a mixed solution and simultaneously adjusting a pH of the mixed solution within a range of 6-10;
  (C) filtering the pH-adjusted mixed solution to obtain a solid catalyst;
  (D) drying the solid catalyst at 70-200° C.; and
  (E) heat-treating the dried solid catalyst at 350-800° C.
 (ii) continuously passing a reactant consisting of a mixed gas of a C4 mixture, air and steam through a catalyst layer supported with the zinc ferrite catalyst to conduct an oxidative dehydrogenation reaction, the C4 mixture comprises 0.5~50 wt % of n-butane, 40~99 wt % of n-butene, and 0.5~10 wt % other than n-butane and n-butene,
 (iii) obtaining 1,3-butadiene from the catalyst layer.

2. The method of preparing 1,3-butadiene according to claim 1, wherein, in (ii), a mixing ratio of n-butene:air:steam in the reactant is 1:0.5~10:1~50.

3. The method of preparing 1,3-butadiene according to claim 1, wherein, in (ii), the oxidative dehydrogenation reaction is conducted at a reaction temperature of 300~600° C. and at a space velocity of 50~5000 $h^{-1}$ based on n-butene.

* * * * *